(12) United States Patent
Adam et al.

(10) Patent No.: US 7,769,134 B1
(45) Date of Patent: Aug. 3, 2010

(54) MEASURING STRAIN OF EPITAXIAL FILMS USING MICRO X-RAY DIFFRACTION FOR IN-LINE METROLOGY

(75) Inventors: Thomas N. Adam, Slingerland, NY (US); Eric C. Harley, Lagrangeville, NY (US); Anita Madan, Danbury, CT (US); Teresa L. Pinto, Wallkill, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/372,104

(22) Filed: Feb. 17, 2009

(51) Int. Cl.
*G01N 23/20* (2006.01)
(52) U.S. Cl. .......................... 378/72; 73/789
(58) Field of Classification Search ............. 378/70–89; 73/789
See application file for complete search history.

(56) References Cited

U.S. PATENT DOCUMENTS

| 5,414,747 A | 5/1995 | Ruud et al. ................... 378/73 |
| 7,264,777 B1 | 9/2007 | Blum et al. ................... 422/69 |
| 2008/0086276 A1 | 4/2008 | Naka et al. ................... 702/43 |

*Primary Examiner*—Courtney Thomas
(74) *Attorney, Agent, or Firm*—Cantor Colburn LLP; Ian MacKinnon (57) ABSTRACT

In a method for use of x-ray diffraction to measure the strain on the top silicon germanium layer of an SOI substrate, the location of the peak diffraction area of an upper silicon layer of the SOI substrate is determined by first determining the peak diffraction area of the upper silicon layer on a reference pad (where the SOI thickness is about 700-900 Angstroms) within a die formed on a semiconductor wafer. The x-ray beam then moves to that location on the pad of interest to be measured and begins the XRD scan on the pad of interest to ultimately determine the strain of the top silicon germanium layer of the pad of interest.

25 Claims, 8 Drawing Sheets

MEASURING STRAIN OF EPITAXIAL FILMS USING MICRO X-RAY DIFFRACTION FOR IN-LINE METROLOGY

BACKGROUND

The present invention relates to semiconductor manufacturing technology, and, more specifically, to measuring strain of epitaxial films in relatively small pads using micro-spot x-ray diffraction for in-line metrology during the semiconductor manufacturing process.

X-ray diffraction (XRD) is commonly used as a viable measuring technique in the research and development of epitaxial deposition processes in semiconductor manufacturing. Until recently, relatively large area sample sizes (e.g., up to several centimeters squared) were required to successfully carry out an XRD measurement due to x-ray signal strength and spot size. However, the development of new systems and, in particular, intense micro-spot XRD sources have enabled the capability of probing modern standard size measurement pads as typically employed in the industry. Typical modern pad sizes range from 50×50 um$^2$ to 500×500 um$^2$ and state-of-the-art x-ray spot dimensions are approximately 70 um (oval shaped—due to sample tilt). This has enabled x-rays to be used for in-line metrology during the semiconductor manufacturing process. Common parameters that are measured using XRD include the strain, concentration and thickness of a doped silicon pad (e.g., Si(1-x)Ge(x), Si(1-x)C(x) where x is the amount of substitutional dopant) that is part of a patterned wafer having a plurality of such pads. Typically the dopant is used to stress the channel of a semiconductor device formed in the wafer. The patterned wafer could be bulk silicon or a silicon-on-insulator (SOI) wafer (needed for high performance devices). Even though the dopant layer may be SiGe, any kind of dopant, e.g., B, C, etc., may be utilized.

However, problems with the modern micro-spot XRD sources include the fact that source intensity is reduced and relatively much longer counting times are usually needed. The measurement of the strain starts with alignment of the wafer to the XRD beam. Bulk silicon wafer alignment of the XRD source to the peak diffraction area of the silicon is straightforward because of the relatively large diffraction signal intensity from the substrate. Alignment for measurement of peak diffraction on SOI wafers, which is important for modern high-performance technologies, is more complicated, depending upon the process used for manufacturing the wafers. SIMOX wafers have top silicon layers that exhibit the same orientation as the substrate, and thus, a substrate alignment of the XRD source is sufficient as a scan set up. On the other hand, bonded SOI wafers inherently can have miscut or relatively slight angular tilt between the handle and the upper silicon wafer before bonding. As a result, the substrate crystal orientation can differ from that of the upper silicon layer by twice the manufacturing tolerance. X-ray diffraction is extremely sensitive to crystal orientation, and a mere alignment of the XRD source to the base silicon substrate peak diffraction area is insufficient. A relatively well-defined routine may be executed to find the location of the SOI peak position of the upper silicon layer (which is located above the buried oxide layer, which itself is located above the relatively thicker bulk silicon substrate layer), after which the system moves to that angular location and begins the scan. However, for SOI devices with upper silicon layers having a thickness starting as low as 150 Angstroms, it becomes extremely difficult to achieve alignment of the x-ray beam for strain measurements since the diffracted intensity is several orders of magnitude lower than that of the bulk silicon.

BRIEF SUMMARY

According to an embodiment of the invention, in a method for use of x-ray diffraction to measure the strain on the top silicon germanium layer of an SOI substrate, the location of the peak diffraction area of an upper silicon layer of the SOI substrate is determined by first determining the peak diffraction area of the upper silicon layer on a reference pad (where the SOI thickness is about 700-900 Angstroms) within a die formed on a semiconductor wafer. The x-ray beam then moves to that location on the pad of interest to be measured and begins the XRD scan on the pad of interest to ultimately determine the strain of the top silicon germanium layer of the pad of interest.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features and advantages of the invention are apparent from the following detailed description in conjunction with the accompanying drawings in which:

DETAILED DESCRIPTION

Figure 1:
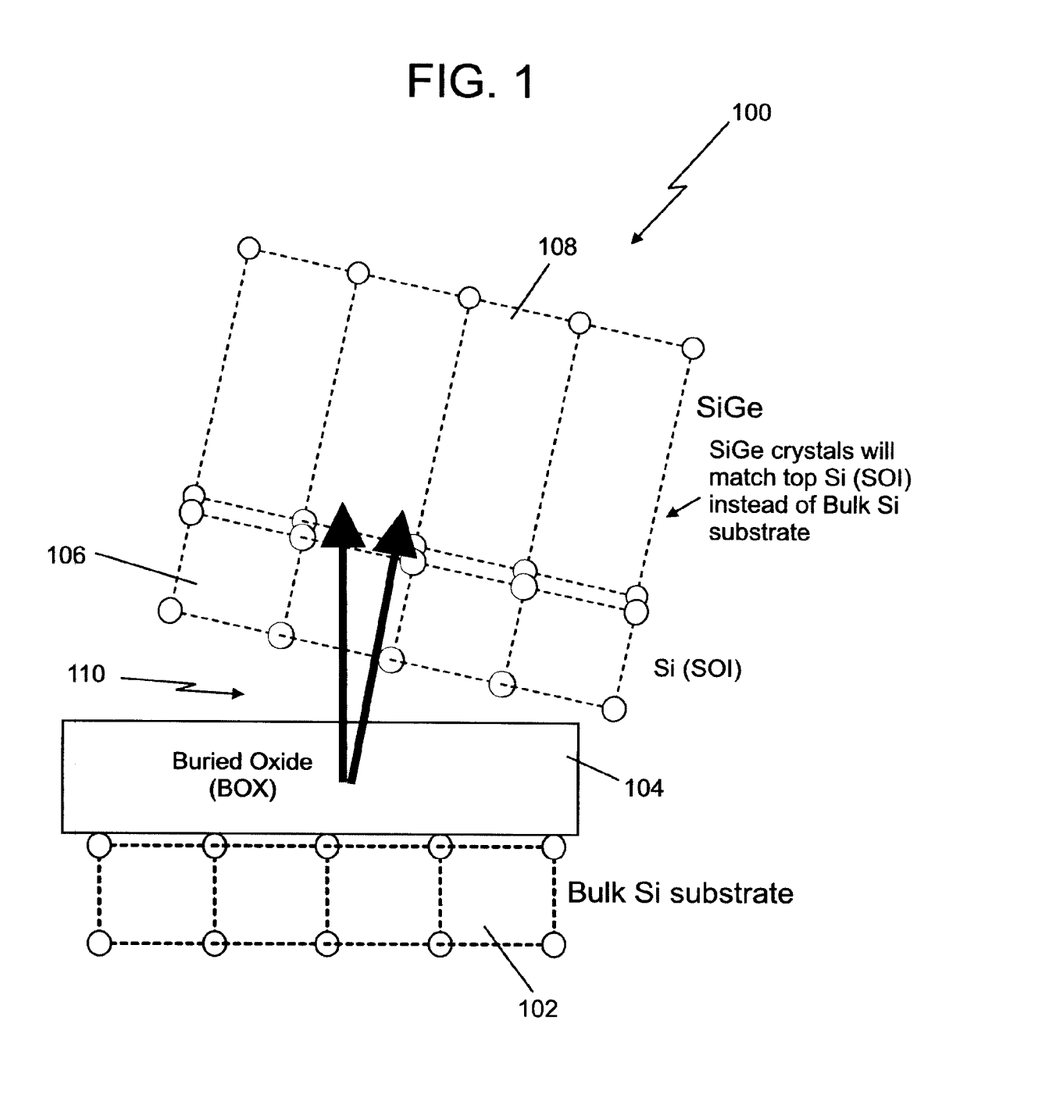
FIG. 1 is a cross-section diagram of a doped silicon layer (in this case Si(1-x)Ge(x)) on a SOI measurement pad located on a die in the SOI wafer.

Referring to FIG. 1, there illustrated is a cross-section diagram of a silicon-on-insulator (SOI) pad 100 formed in a wafer. The SOI pad 100 comprises a lower bulk substrate silicon layer 102 above which is located a buried oxide (BOX) layer 104. Located above the BOX layer 104 is an upper layer 106 of silicon in which, for example, components of transistors (e.g., FETs) are ultimately formed in the SOI pad 100 during the semiconductor device manufacturing process. Above the top silicon layer 106 is a top layer 108 of silicon germanium also in which components (e.g., drain, source) of the FET transistors are formed.

In modern SOI semiconductor devices, the thickness of the bulk or lower silicon layer 102 may be approximately 0.7 cm. In contrast, the thickness of the upper silicon layer 106 may be as small as approximately 150 Angstroms. An inherent miscut or tilt angle 110 exists between the upper and lower silicon layers 102, 106 in SOI semiconductor device technology. FIG. 1 illustrates an exaggerated amount of miscut 110. In actuality, the miscut or tilt angle 110 is on the order of approximately one third of an angular degree. FIG. 1 also notes that the crystals of the top silicon germanium layer 108 align or match with those of the upper silicon layer 106 instead of the bottom bulk silicon layer 102. The thickness of the top SiGe layer 108 may be approximately 400-600 Angstroms.

Figure 2:
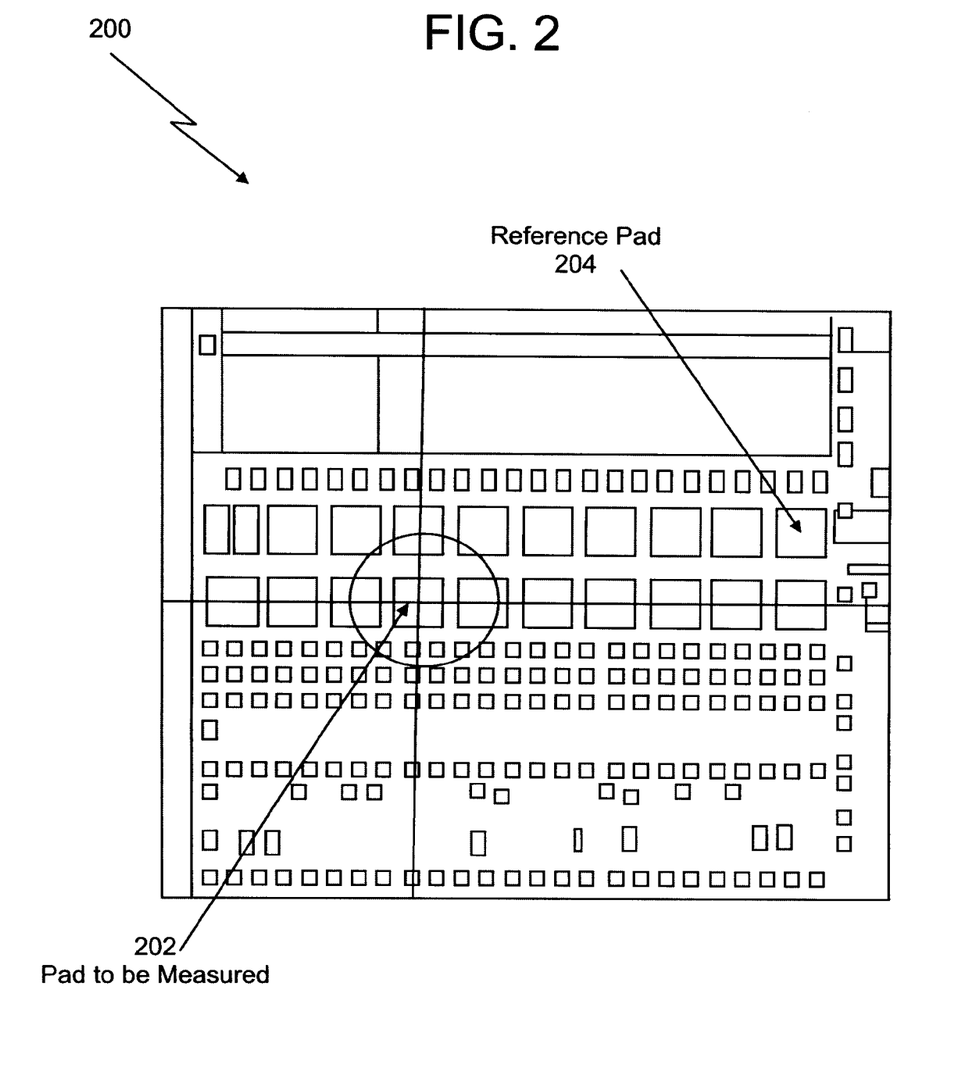
FIG. 2 is a portion of an SOI semiconductor wafer during a point in the manufacturing process of that wafer.

Referring to FIG. 2, there illustrated is a portion of an SOI semiconductor wafer 200 during a point in the manufacturing process of that wafer. The wafer 200 may have approximately 50 chips formed on the wafer, and each chip may have between 10-20 pads. One of the pads comprises a pad of interest 202 to be measured by XRD for certain characteristics, including the strain of the top SiGe layer 108 (FIG. 1). The thickness of the upper silicon layer 106 may be approximately 150 Angstroms. Another one of the pads may comprise a reference pad 204 in which the upper silicon layer 106 may have a thickness of approximately 700 Angstroms, and no top silicon germanium layer 108 exists on this pad 204.

Typically, when using x-ray diffraction during in-line metrology (i.e., at a certain point or step within the overall SOI semiconductor device manufacturing process), only one of the pads (not the reference pad 204) within a chip is utilized for XRD in determining the various characteristics (e.g., strain, thickness concentration, etc.) of one or more layers of that pad. During the conventional XRD process on this pad of interest 202, the XRD beam is focused on the pad 202 to be measured and the beam is moved until it is aligned with the peak or largest amount of diffraction corresponding to the bulk silicon layer 102. The amount of diffraction, including the peak amount, is determined in a conventional manner using a common XRD diffractor meter, which provides a visual graphical display (reference number 300 in FIG. 3, for example) of the amount of diffraction of the x-ray beam (measurement is in Reciprocal Space which is related to the angle of incidence and diffraction of the beam). The graphical display 300 resembles a topographical map to some extent in indicating the relative amounts or intensities of diffraction, typically in different colors.

Figure 3:
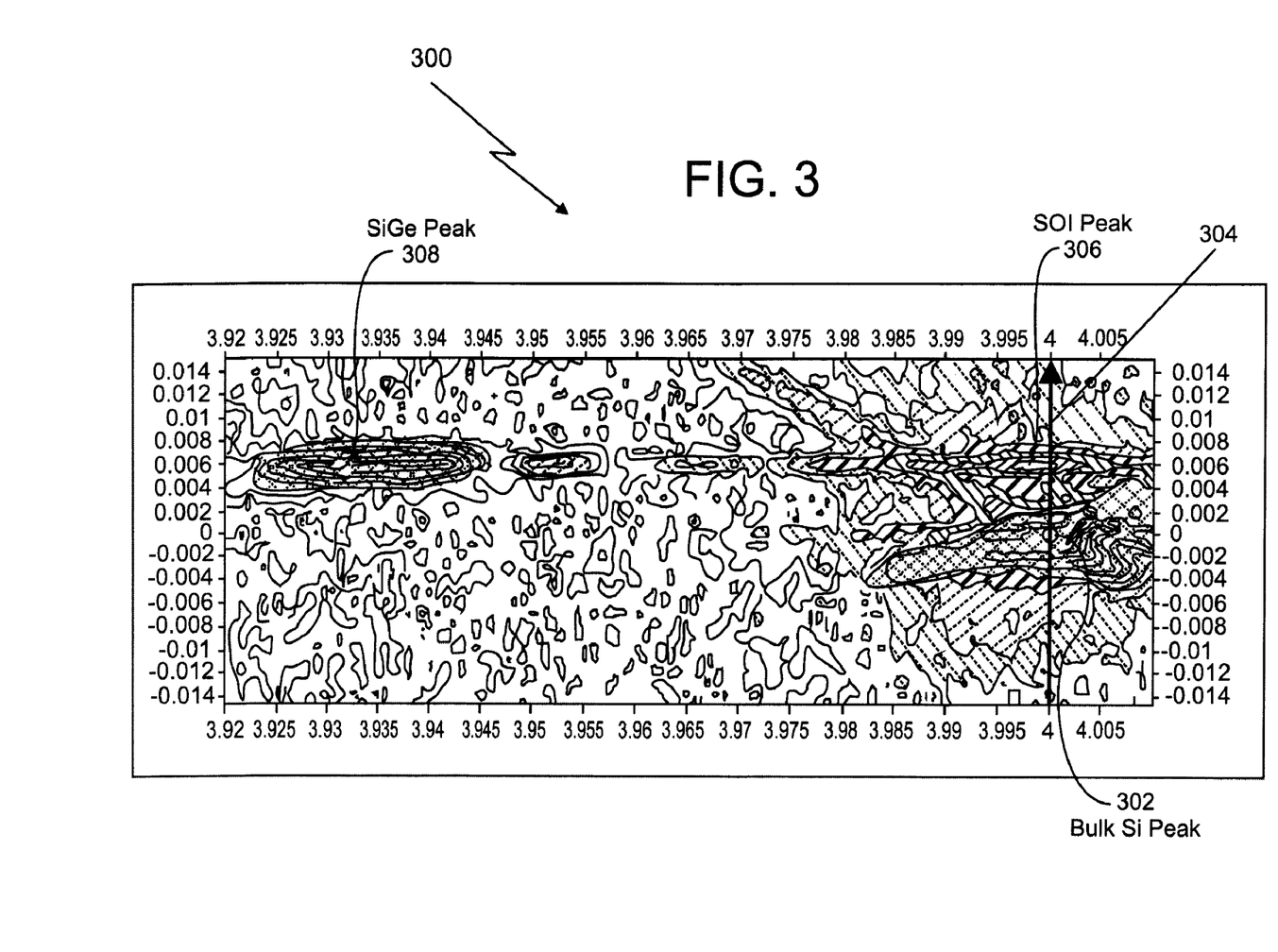
FIG. 3 is a graphical display of the amount of diffraction of an x-ray beam at different points in Reciprocal Space (typical units used in XRD measurements)

The graphical display 300 of FIG. 3 also illustrates a portion of the steps carried out by the conventional technique of measuring the strain on the top SiGe layer 108 (FIG. 1) of the SOI semiconductor pad 100. That technique involves use of only the pad of interest 202 to be measured and makes no use of the reference pad 204. In a step, the XRD beam is focused on the pad of interest 202 and the XRD beam is aligned to locate the peak amount of diffraction 302 of the bulk silicon layer 102. A vertical line 304 with an arrowhead is drawn through the location of the peak amount of diffraction 302 of the bulk silicon layer 102. Next a rocking curve is performed (i.e., the wafer is moved on its own axis) on the vertical line 304 in an attempt to locate the peak amount of diffraction 306 of the upper silicon layer 106. In this example of the conventional technique for measuring the strain on the upper silicon layer 106, FIG. 3 illustrates that the vertical line 304 is drawn through both the peak amount of diffraction (Bulk Si Peak) 302 of the bulk silicon layer 102 and the peak amount of diffraction (SOI Peak) 306 of the upper silicon layer 106.

Next, a scan is performed by drawing a horizontal line (FIG. 6) and moving along that line to the left to locate the peak amount of diffraction 308 of the top SiGe layer 108 (FIG. 1) on the pad of interest 202. It is then known to calculate the strain of the upper silicon layer 106 of an SOI pad 100 using the measured distance between the peak amount of diffraction 304 of the upper silicon layer 106 and the peak amount of diffraction 308 of the top silicon germanium layer 108.

Problems with this approach include the fact that it is inherently difficult to locate the peak amount of diffraction 304 of the upper silicon layer 106. This is because of the relatively thin upper silicon layer (e.g., 150-200 Angstroms). Also, if the miscut 110 is relatively large, it may be impossible to locate the peak amount of diffraction 304 of the upper silicon layer 106. On the other hand, if the amount of miscut is relatively small, then it is difficult to determine the peak amount of diffraction of the upper silicon layer 106. On the other hand, if the amount of miscut is relatively large, the time needed to scan the XRD beam and locate the peak amount of diffraction of the upper silicon layer 106 is also relatively large (e.g., ten minutes). This amount of time undesirably slows down the overall in-line strain metrology of the SOI semiconductor device manufacturing process where speed of measurement is an essence. An additional problem with the conventional approach (particularly for relatively small amounts of miscut 110) is that the peak amount of diffraction of the upper silicon layer 106 comprises a "shoulder" or smaller amount of intensity on the signal curve that also illustrates the peak amount of diffraction of the bulk silicon layer 102, where that peak amount of intensity of the bulk silicon layer 102 is greater that that of the upper silicon layer 106. Due to this fact, it may be difficult, if not impossible, to separate the two diffraction peaks, which can lead to errors in determining various other parameters, for example, an estimation of the concentration of germanium within the pad of interest 202.

Still referring to FIGS. 2 and 3, an embodiment of the invention determines the strain on the top SiGe layer 108 of the SOI semiconductor pad 100 by using not only the pad of interest 202 but also the reference pad 204. In a method embodiment for use of x-ray diffraction to measure the strain on the top SiGe layer 108 of an SOI pad 100, the location of the peak diffraction area of the upper silicon layer 106 is determined by first determining the peak diffraction area 304 of the upper silicon layer 106 on the reference pad 204 and not on the pad of interest 202. This is performed by focusing the X-ray beam on the reference pad 204 and aligning the XRD diffractor meter on the location of the peak amount of diffraction 302 of the bulk silicon layer 102. Then, following the vertical line 304 upwards in FIG. 3, the peak amount of diffraction 306 of the upper silicon layer 106 is located relatively more easily than with the conventional method described above. This is because the thickness of the upper silicon layer 106 of the reference pad 204 is approximately 700 Angstroms, which is relatively much thicker than the thickness of approximately 180 Angstroms of the same layer 106 on the pad of interest 202. This leads to a relatively greater intensity for the peak of diffraction 306 of the upper silicon layer 106 on the reference pad 204, thereby making it easier to locate.

Figure 4:
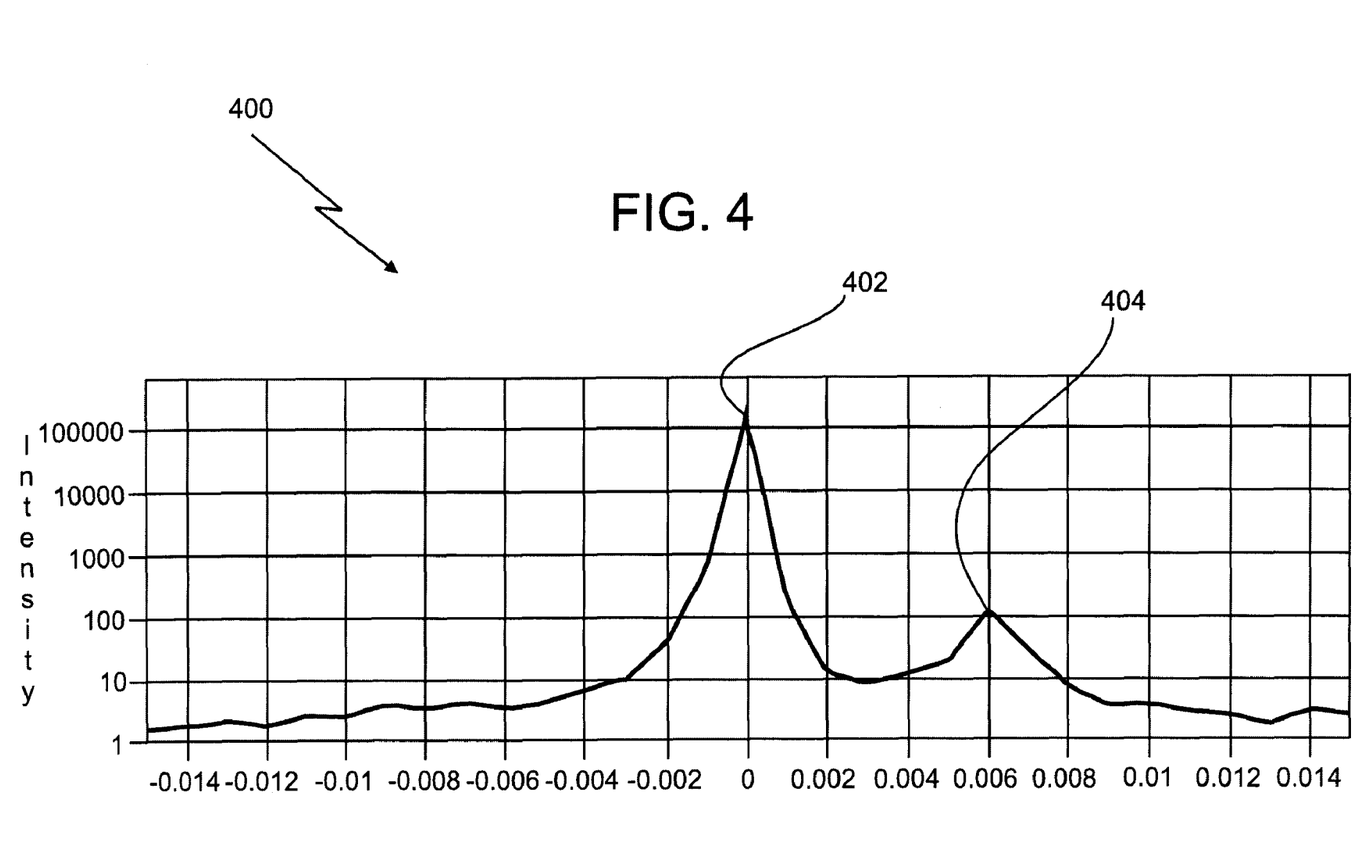
FIG. 4 is a graph showing the peak of diffraction of a bulk silicon layer and a peak of diffraction of an upper silicon layer within an SOI semiconductor pad.

FIG. 4 illustrates a graph 400 showing the peak of diffraction 402 of the bulk silicon layer 102 and the peak of diffraction 404 of the upper silicon layer 106. From this graph 400 it can be seen that the two peaks of diffraction 402, 404 are easily discerned and distinguished from one another primarily because they are separated relatively widely enough from each other. Also, the peak of diffraction 404 of the upper silicon layer 106 is greater in intensity than in the conventional method described above, which is also due to the greater thickness of the upper silicon layer in the reference pad 204 as compared to that of the pad of interest 202.

Figure 5:
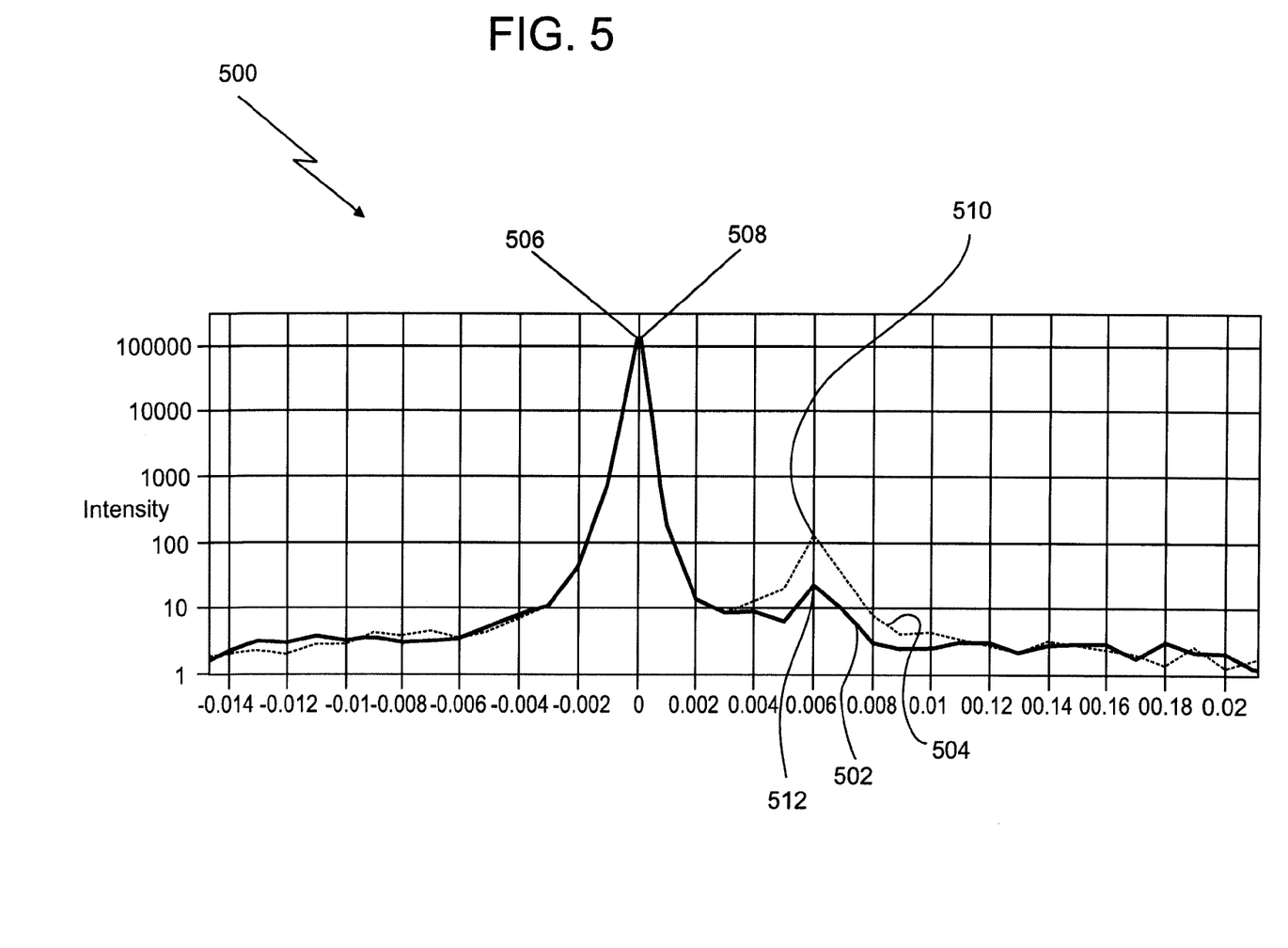
FIG. 5 is a comparison of the peaks of diffraction of a bulk silicon layer and of the upper silicon (SOI) layer from a reference pad and a pad to be measured.

Referring to FIG. 5, there illustrated is a graph 500 of two curves (solid line 502, dotted line 504) showing the peaks of diffraction of a bulk silicon layer 102 and of an upper silicon layer 106, respectively, for a pad of interest 202 and a reference pad 204. From the graph 500 of FIG. 5, it can be seen that the peaks of diffraction 506, 508 of the bulk silicon layer 102 for both the pad of interest 202 (i.e., the pad to be measured) and the reference pad 204 are approximately equal, which is the case as the thickness of the bulk silicon layer 102 is approximately the same for both pads 202, 204. The primary difference in the graph 500 of FIG. 5 is the intensity or magnitude of the peaks of diffraction 510, 512 of the upper silicon layer 106 (FIG. 1). The peak of diffraction 510 of the upper silicon layer of the reference pad 204 is greater than the peak of diffraction 512 of the upper silicon layer of the pad of interest 202 because of the greater thickness (700 A) of the former versus the latter (150 A).

Figure 6:
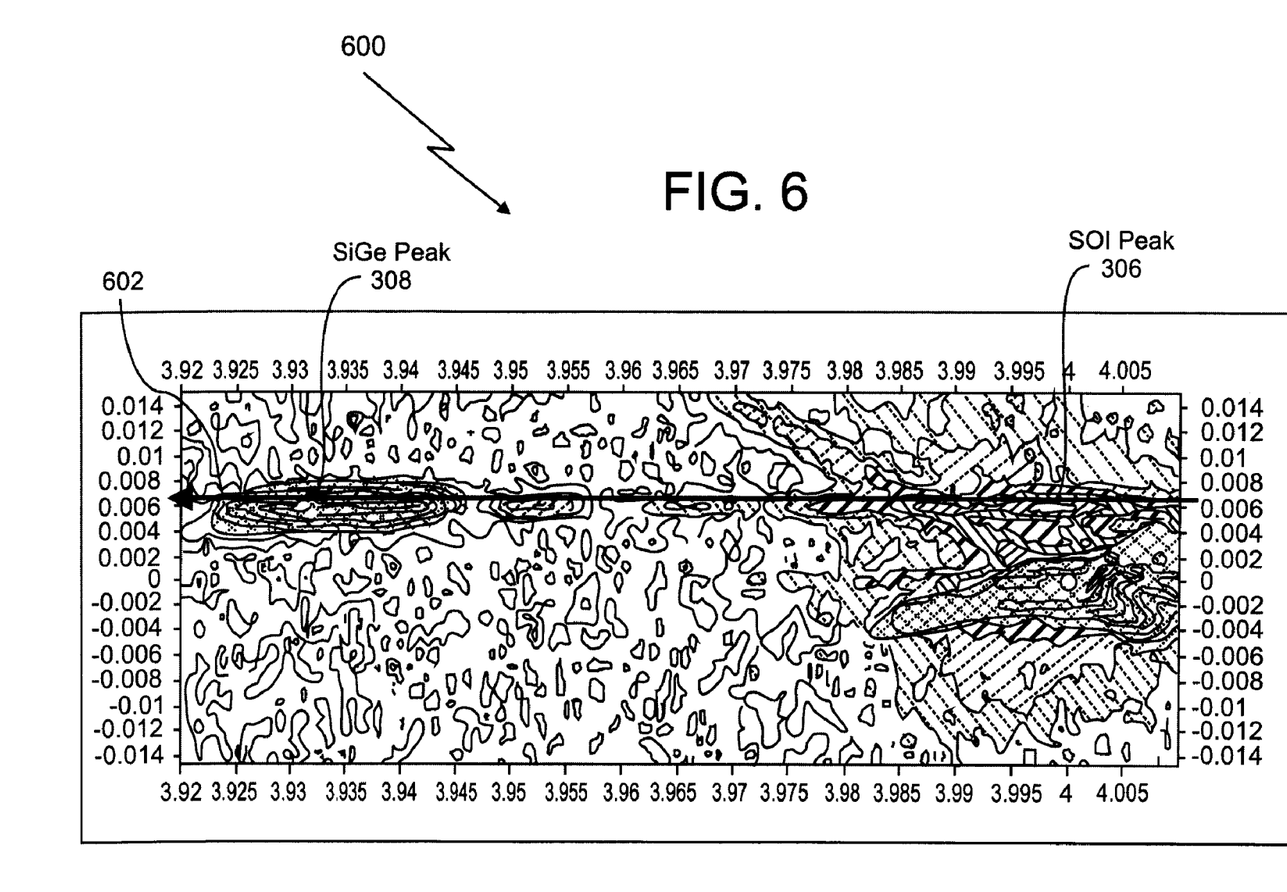
FIG. 6 is a graphical display of the amount of diffraction of an x-ray beam at different points in Reciprocal Space (typical units used in XRD measurement) showing the different scans that need to be done to obtain the required parameters.
Figure 7:
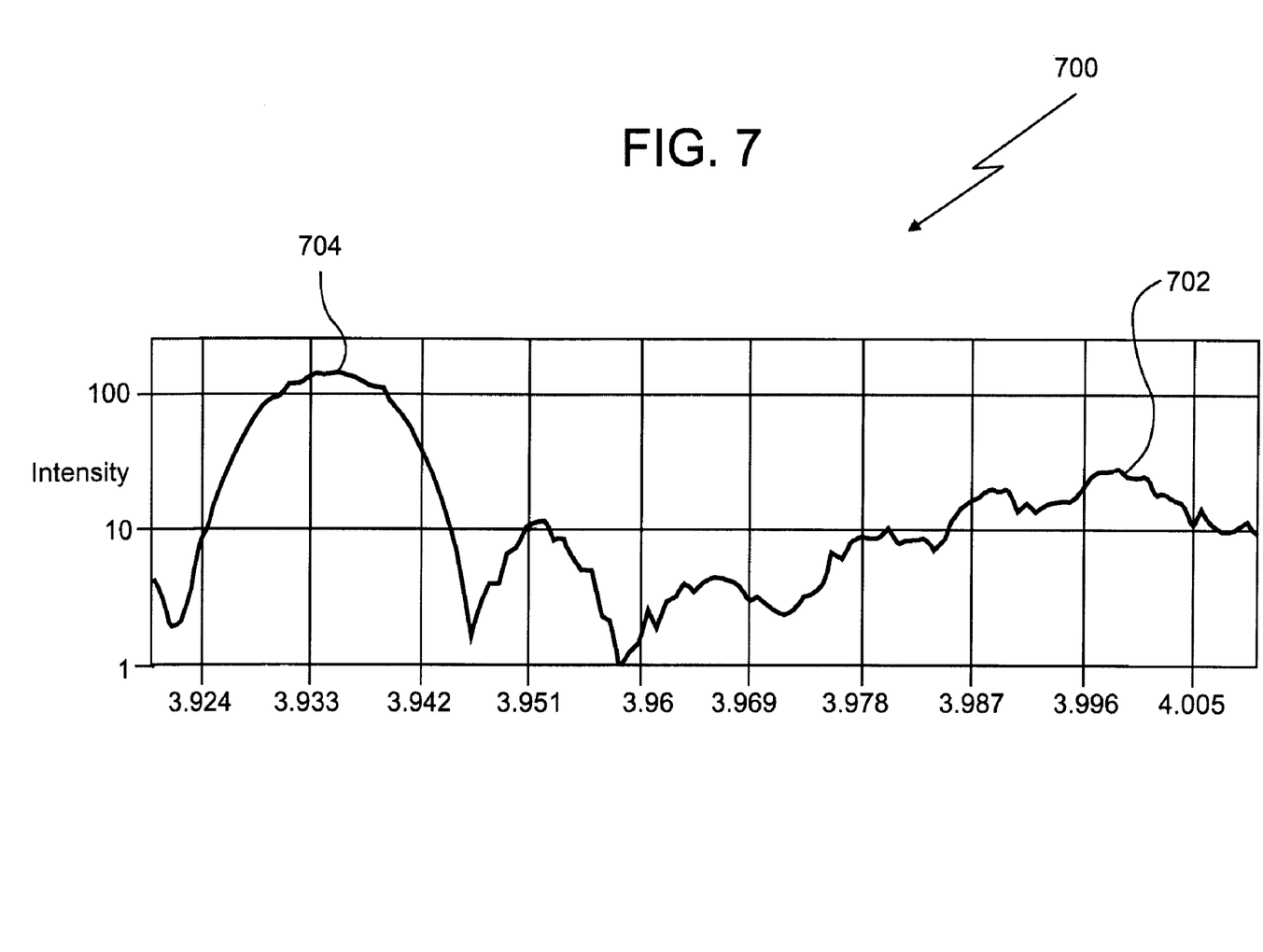
FIG. 7 is a graph showing the peak of diffraction of a top silicon germanium layer and a peak of diffraction of an upper silicon layer within an SOI semiconductor device.

Referring to FIG. 6, there illustrated is a graphical display 600 (similar to FIG. 3) of the amount of diffraction of the x-ray beam at various locations on the pad of interest 202. Once the peak of diffraction 306 of the upper silicon layer 106 has been located on the reference pad 204 as described above in connection with FIG. 3, the x-ray beam is then moved to that location on the pad of interest 202. The XRD scan on the pad of interest 202 is then started to locate the peak of diffraction 308 of the top silicon germanium layer 108 on the pad of interest 202. Then, using the distance between these two peaks of diffraction along the horizontal line 602 with the arrowhead, the amount of strain on the top silicon germanium layer 108 on the pad of interest 202 may be determined using conventional, known calculations. Other parameters (e.g., concentration, thickness, etc.) of the top silicon germanium layer or other epitaxial layers (e.g., SiC, etc.) on the SOI device 100 may be determined using the method embodiments of the invention, and in a relatively much quicker time frame. FIG. 7 is a graph 700 showing the peak of diffraction 702 of the upper silicon layer 106 and a peak of diffraction 704 of the top silicon germanium layer 108 within an SOI semiconductor pad 100.

Figure 8:
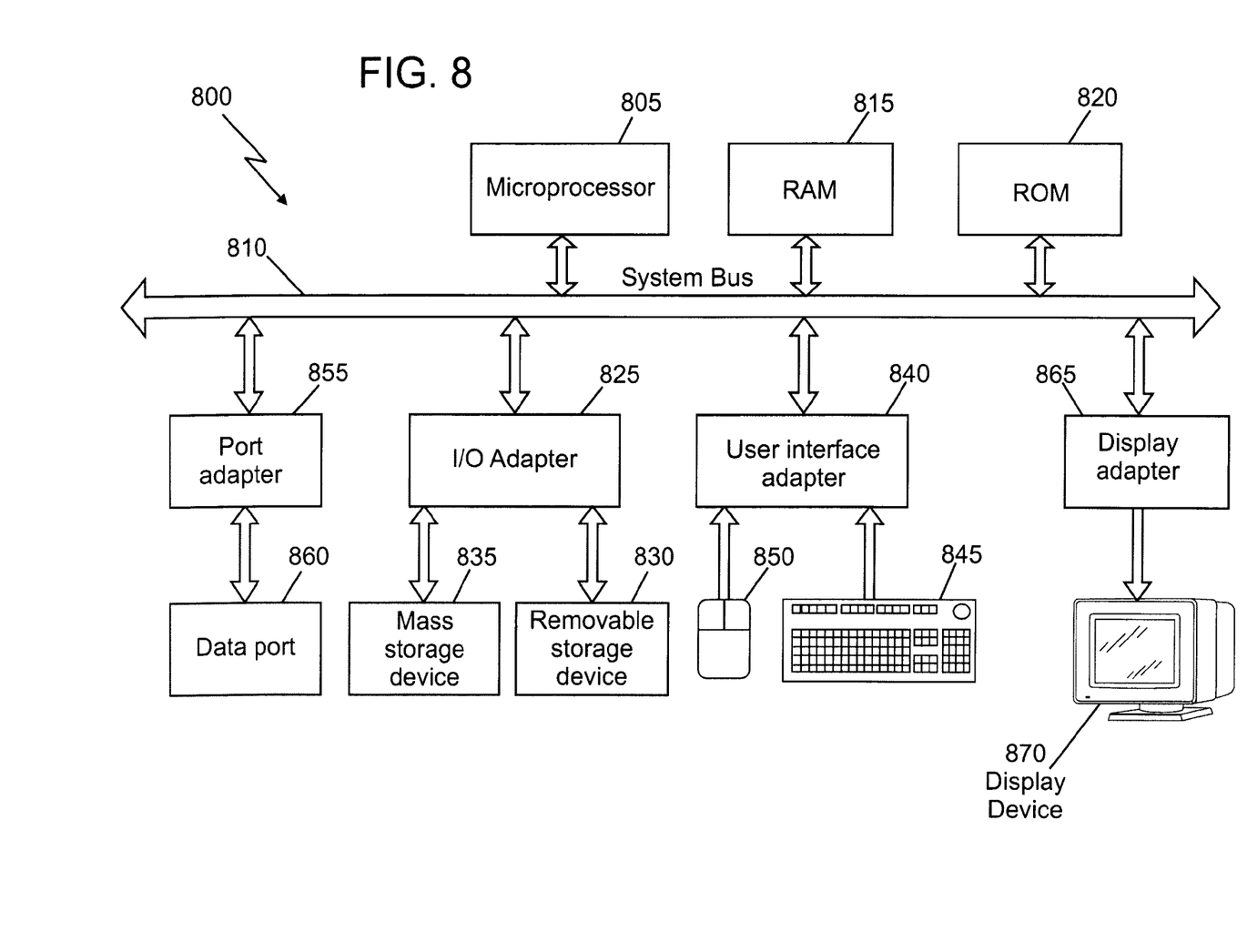
FIG. 8 is a schematic block diagram of a general-purpose computer suitable for practicing embodiments of the present invention.

Generally, the method embodiments of the invention may be practiced with a commercially available XRD diffractor meter, which may comprise a computer, for example, a general-purpose computer, and the method may be coded as a set of instructions on removable or hard media for use by the computer. FIG. 8 is a schematic block diagram of a computer suitable for practicing embodiments of the present invention. In FIG. 8, computer system 800 has at least one microprocessor or central processing unit (CPU) 805. CPU 805 is interconnected via a system bus 810 to a random access memory (RAM) 815, a read-only memory (ROM) 820, an input/output (I/O) adapter 825 for a connecting a removable data and/or program storage device 830 and a mass data and/or program storage device 835, a user interface adapter 840 for connecting a keyboard 845 and a mouse 850, a port adapter 855 for connecting a data port 860 and a display adapter 865 for connecting a display device 870.

ROM 820 contains the basic operating system for computer system 800. The operating system may alternatively reside in RAM 815 or elsewhere as is known in the art. Examples of removable data and/or program storage device 830 include magnetic media such as floppy drives and tape drives and optical media such as CD ROM drives. Examples of mass data and/or program storage device 835 include hard disk drives and non-volatile memory such as flash memory. In addition to keyboard 845 and mouse 850, other user input devices such as trackballs, writing tablets, pressure pads, microphones, light pens and position-sensing screen displays may be connected to user interface 840. Examples of display devices include cathode-ray tubes (CRT) and liquid crystal displays (LCD).

A computer program with an appropriate application interface may be created by one of skill in the art and stored on the system or a data and/or program storage device to simplify the practicing of this invention. In operation, information for or the computer program created to run the present invention is loaded on the appropriate removable data and/or program storage device 830, fed through data port 860 or typed in using keyboard 845.

In view of the above, the present method embodiments may therefore take the form of computer or controller implemented processes and apparatus for practicing those processes. The disclosure can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to implement the exemplary method described above.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method for determining an amount of strain on a portion of a semiconductor device, comprising:
   determining a location of a peak of diffraction within a first layer of the semiconductor device on a reference pad;
   determining a location of a peak of diffraction within a second layer of the semiconductor device on the reference pad;
   determining a location of a peak of diffraction within a third layer of the semiconductor device on a pad of interest, wherein the pad of interest is different than the reference pad; and
   calculating the amount of strain within the third layer of the semiconductor device on the pad of interest from the determined location of the peak of diffraction within the second layer of the semiconductor device on the reference pad and from the determined location of the peak of diffraction within the third layer of the semiconductor device on the pad of interest.

2. The method of claim 1, wherein determining a location of a peak of diffraction within a first layer of the semiconductor device on a reference pad comprises using x-ray diffraction.

3. The method of claim 1, wherein determining a location of a peak of diffraction within a second layer of the semiconductor device on the reference pad comprises using x-ray diffraction.

4. The method of claim 1, wherein determining a location of a peak of diffraction within a third layer of the semiconductor device on a pad of interest comprises using x-ray diffraction.

5. The method of claim 1, wherein determining a location of a peak of diffraction within a second layer of the semiconductor device on the reference pad comprises using x-ray diffraction, wherein using x-ray diffraction comprises focusing an x-ray beam on the second layer of the semiconductor device on the reference pad and determining the location of the peak of diffraction within the second layer of the semiconductor device on the reference pad using a display of the diffraction within the second layer.

6. The method of claim 5, further comprising after determining the location of the peak of diffraction within the second layer of the semiconductor device on the reference pad, then focusing the x-ray beam on a similar location using the determined location of a peak of diffraction within a second layer on the pad of interest to then determine the location of the peak of diffraction within the third layer of the semiconductor device on the pad of interest.

7. The method of claim 6, wherein calculating the amount of strain within a third layer of the semiconductor device on the pad of interest comprises calculating the amount of strain using a distance between the location of the peak of diffraction within the second layer of the semiconductor device on the pad of interest and the location of the peak of diffraction within the third layer of the semiconductor device on the pad of interest.

8. A computer program product, comprising:
   a computer-readable computer program code for determining an amount of strain on a portion of a semiconductor device; and
   instructions for causing a computer to implement a method, the method further including
   determining a location of a peak of diffraction within a first layer of the semiconductor device on a reference pad;
   determining a location of a peak of diffraction within a second layer of the semiconductor device on the reference pad;
   determining a location of a peak of diffraction within a third layer of the semiconductor device on a pad of interest, wherein the pad of interest is different than the reference pad; and
   calculating the amount of strain within the third layer of the semiconductor device on the pad of interest from the determined location of the peak of diffraction within the second layer of the semiconductor device on the reference pad and from the determined location of the peak of diffraction within the third layer of the semiconductor device on the pad of interest.

9. The computer program product of claim 8, wherein determining a location of a peak of diffraction within a first layer of the semiconductor device on a reference pad comprises using x-ray diffraction.

10. The computer program product of claim 8, wherein determining a location of a peak of diffraction within a second layer of the semiconductor device on the reference pad comprises using x-ray diffraction.

11. The computer program product of claim 8, wherein determining a location of a peak of diffraction within a third layer of the semiconductor device on a pad of interest comprises using x-ray diffraction.

12. The computer program product of claim 8, wherein determining a location of a peak of diffraction within a second layer of the semiconductor device on the reference pad comprises using x-ray diffraction, wherein using x-ray diffraction comprises focusing an x-ray beam on the second layer of the semiconductor device on the reference pad and determining the location of the peak of diffraction within the second layer of the semiconductor device on the reference pad using a display of the diffraction within the second layer.

13. The computer program product of claim 12, further comprising after determining the location of the peak of diffraction within the second layer of the semiconductor device on the reference pad, then focusing the x-ray beam on a similar location within a second layer on the pad of interest to then determine the location of the peak of diffraction within the third layer of the semiconductor device on the pad of interest.

14. The computer program product of claim 13, wherein calculating the amount of strain within a third layer of the semiconductor device on the pad of interest comprises calculating the amount of strain using a distance between the location of the peak of diffraction within the second layer of the semiconductor device on the pad of interest and the location of the peak of diffraction within the third layer of the semiconductor device on the pad of interest.

15. A system for determining an amount of strain on a portion of a semiconductor device, comprising:
   a computing network including a processing device in communication with one or more computer memory storage devices; and the computing network further configured to implement a method for determining an amount of strain on a portion of a semiconductor device, the method further including determining a location of a peak of diffraction within a first layer of the semiconductor device on a reference pad;

determining a location of a peak of diffraction within a second layer of the semiconductor device on the reference pad;

determining a location of a peak of diffraction within a third layer of the semiconductor device on a pad of interest, wherein the pad of interest is different than the reference pad; and calculating the amount of strain within the third layer of the semiconductor device on the pad of interest from the determined location of the peak of diffraction within the second layer of the semiconductor device on the reference pad and from the determined location of the peak of diffraction within the third layer of the semiconductor device on the pad of interest.

16. The system of claim 15, wherein determining a location of a peak of diffraction within a first layer of the semiconductor device on a reference pad comprises using x-ray diffraction.

17. The system of claim 15, wherein determining a location of a peak of diffraction within a second layer of the semiconductor device on the reference pad comprises using x-ray diffraction.

18. The system of claim 15, wherein determining a location of a peak of diffraction within a third layer of the semiconductor device on a pad of interest comprises using x-ray diffraction.

19. The system of claim 15, wherein determining a location of a peak of diffraction within a second layer of the semiconductor device on the reference pad comprises using x-ray diffraction, wherein using x-ray diffraction comprises focusing an x-ray beam on the second layer of the semiconductor device on the reference pad and determining the location of the peak of diffraction within the second layer of the semiconductor device on the reference pad using a display of the diffraction within the second layer.

20. The system of claim 19, further comprising after determining the location of the peak of diffraction within the second layer of the semiconductor device on the reference pad, then focusing the x-ray beam on a similar location within a second layer on the pad of interest to then determine the location of the peak of diffraction within the third layer of the semiconductor device on the pad of interest.

21. The system of claim 20, wherein calculating the amount of strain within a third layer of the semiconductor device on the pad of interest comprises calculating the amount of strain using a distance between the location of the peak of diffraction within the second layer of the semiconductor device on the pad of interest and the location of the peak of diffraction within the third layer of the semiconductor device on the pad of interest.

22. A method for determining an amount of strain on a top silicon germanium layer of a silicon-on-insulator (SOI) semiconductor device, comprising:

determining a location of a peak of diffraction within a bulk silicon substrate layer of the SOI semiconductor device on a reference pad;

determining a location of a peak of diffraction within an upper silicon layer of the SOI semiconductor device on the reference pad;

determining a location of a peak of diffraction within the top silicon germanium layer of the SOI semiconductor device on a pad of interest, wherein the pad of interest is different than the reference pad; and calculating the amount of strain within the top silicon germanium layer of the SOI semiconductor device on the pad of interest from the determined location of the peak of diffraction within the upper silicon layer of the SOI semiconductor device on the reference pad and from the determined location of the peak of diffraction within the top silicon germanium layer of the SOI semiconductor device on the pad of interest.

23. The method of claim 22, wherein each step of determining comprises using x-ray diffraction.

24. The method of claim 22, wherein determining a location of a peak of diffraction within an upper silicon layer of the SOI semiconductor device on the reference pad comprises using x-ray diffraction, wherein using x-ray diffraction comprises focusing an x-ray beam on the upper silicon layer of the SOI semiconductor device on the reference pad and determining the location of the peak of diffraction within the upper silicon layer of the SOI semiconductor device on the reference pad using a display of the diffraction within the second layer, and further comprising after determining the location of the peak of diffraction within the upper silicon layer of the SOI semiconductor device on the reference pad, then focusing the x-ray beam on a similar location within an upper silicon layer on the pad of interest to then determine the location of the peak of diffraction within the top silicon germanium layer of the SOI semiconductor device on the pad of interest.

25. The method of claim 24, wherein calculating the amount of strain within the top silicon germanium layer of the SOI semiconductor device on the pad of interest comprises calculating the amount of strain using a distance between the location of the peak of diffraction within the upper silicon layer of the SOI semiconductor device on the pad of interest and the location of the peak of diffraction within the top silicon germanium layer of the SOI semiconductor device on the pad of interest.

* * * * *